United States Patent [19]
Muench et al.

[11] Patent Number: 6,155,116
[45] Date of Patent: Dec. 5, 2000

[54] ACOUSTIC TREATMENT PERFORMANCE TESTING

[75] Inventors: John D. Muench, East Greenwich; Pierre J. Corriveau; Paul W. Wynn, both of Portsmouth, all of R.I.

[73] Assignee: The United States of America as represented by the Secretary of the Navy, Washington, D.C.

[21] Appl. No.: 09/416,133

[22] Filed: Oct. 4, 1999

[51] Int. Cl.$^7$ .................................................. G01N 29/00
[52] U.S. Cl. ........................ 73/599; 73/574; 73/575; 73/866
[58] Field of Search .................... 73/570, 574, 575, 73/599, 866

[56] References Cited

U.S. PATENT DOCUMENTS

| | | | |
|---|---|---|---|
| 3,589,174 | 6/1971 | Bauke | 73/575 |
| 4,577,503 | 3/1986 | Imaino et al. | 73/602 |
| 5,143,072 | 9/1992 | Kantorvich et al. | 73/599 |

*Primary Examiner*—Richard A. Moller
*Attorney, Agent, or Firm*—Michael J. McGowan; James M. Kasischke; Prithvi C. Lall

[57] ABSTRACT

A method and system for acoustic treatment performance testing in a free-field acoustic environment is provided. A sound source directs a gated acoustic pulse at an acoustic treatment. Acoustic pressures of the gated acoustic pulse and reflected energy from the acoustic treatment are measured from a location approximately in-line with the source and the acoustic treatment. This measurement location is at least one-half the wavelength of the frequency of interest away from the source and is at least a distance equal to (t*c/2) away from the acoustic treatment where t is equal to the duration of the gated acoustic pulse and c is equal to the speed of sound in the free-field acoustic environment. The acoustic pressures of the gated acoustic pulse and reflected energy are compared as an indication of performance of the acoustic treatment at a frequency of interest.

14 Claims, 1 Drawing Sheet

ACOUSTIC TREATMENT PERFORMANCE TESTING

STATEMENT OF GOVERNMENT INTEREST

The invention described herein may be manufactured and used by or for the Government of the United States of America for Governmental purposes without the payment of any royalties thereon or therefor.

BACKGROUND OF THE INVENTION

(1) Field of the Invention

The present invention relates generally to acoustic performance testing, and more particularly to a method and system for testing the performance of an acoustic treatment in a free-field acoustic environment across a broad frequency range that can include high frequencies up to at least 40,000 hertz.

(2) Description of the Prior Art

Standard acoustic performance testing methodologies describe procedures to assure low frequency acoustic performance. These methods, described in ANSI/ASTM C384-77, present techniques to determine the low frequency cut-off of a material, geometry or shape. Low frequency verification of acoustic performance is experimentally determined using an impedance tube which allows accurate measurement of incident and reflected sound only at low frequencies. However, no high-frequency (i.e., approximately 16 KHz to 40 KHz) acoustic performance testing methodologies exist even though it is important to design and test the performance of materials over the complete bandwidth of interest.

Anechoic chambers are designed to emulate a free-field environment in which all airborne propagating sound energy is absorbed by acoustic treatment installed on the walls of the chamber. The acoustic treatment which is usually wedge shaped, traps an incident sound wave and dissipates the sound energy as heat. In modest size anechoic chambers, the acoustic treatment is required to absorb sound energy from 80 Hz to 40,000 Hz. However, as mentioned above, studies of acoustic absorption material are generally focused on low frequency performance with the assumption that acceptable high frequency performance is inherent in the material selection and is not affected by geometrical design.

SUMMARY OF THE INVENTION

Accordingly, it is an object of the present invention to provide for the performance testing of an acoustic material or treatment over a broad range of frequencies that includes high frequencies.

Another object of the present invention is to provide for the high-frequency performance testing of acoustic panels to be used in an anechoic chamber.

Still another object of the present invention is to provide for the in-situ, high-frequency acoustic dissipation performance testing of an acoustic treatment.

Other objects and advantages of the present invention will become more obvious hereinafter in the specification and drawings.

In accordance with the present invention, acoustic treatment performance testing is accomplished in a free-field acoustic environment. An acoustic treatment to be tested is disposed in the free-field acoustic environment. A gated acoustic pulse having a frequency of interest is generated from a source within the free-field acoustic environment. The gated acoustic pulse is focused at the acoustic treatment. As a result, the gated acoustic pulse is partially reflected from the acoustic treatment as reflected energy in the free-field acoustic environment. Acoustic pressure of the gated acoustic pulse focused at the acoustic treatment and the reflected energy is measured from a location approximately in-line with the source and the acoustic treatment. This measurement location is at least one-half the wavelength of the frequency of interest away from the source and is at least a distance equal to (t*c/2) away from the acoustic treatment where t is equal to the duration of the gated acoustic pulse and c is equal to the speed of sound in the free-field acoustic environment. The acoustic pressure of the reflected energy is compared to the acoustic pressure of the gated acoustic pulse as an indication of performance of the acoustic treatment at the frequency of interest.

BRIEF DESCRIPTION OF THE DRAWINGS

Other objects, features and advantages of the present invention will become apparent upon reference to the following description of the preferred embodiments and to the drawings, wherein corresponding reference characters indicate corresponding arts throughout the several views of the drawings and wherein.

DESCRIPTION OF THE PREFERRED EMBODIMENT(S)

Figure 1:
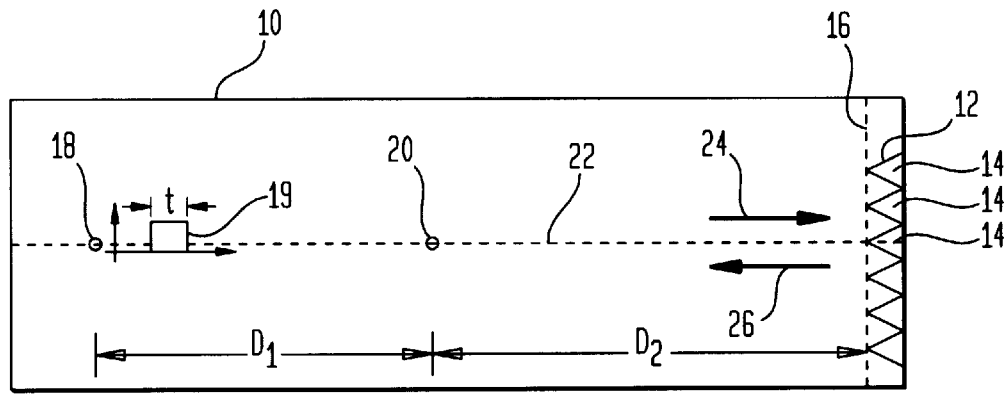
FIG. 1 is a schematic view of a test setup used to carry out acoustic performance testing according to an embodiment of the present invention.

Referring now to the drawings, and more particularly to FIG. 1, a test setup used to carry out acoustic performance testing is shown schematically. In general, the present invention is used to evaluate the acoustic performance of any acoustic material or treatment. In order to isolate the acoustic treatment under test from unwanted acoustic reflection and/or absorption, it is desirable to test the treatment in a free-field acoustic environment. Accordingly, by way of example, the test setup is contained within such a free-field acoustic environment indicated by boundary lines 10. Practically speaking, boundary lines 10 define the confines of an anechoic chamber, designs of which are well known in the art.

The acoustic treatment can be any material, shape or combination of materials and shapes. In the illustrated example, the acoustic treatment indicated at 12 is a panel constructed of foam wedges 14. Tips of wedges 14 define a plane referenced by dashed line 16. Acoustic treatment 12 can be incorporated to form a portion of the free-field acoustic environment 10, i.e., the wall of the anechoic chamber.

Positioned in environment 10 are an acoustic signal source 18 capable of outputting acoustic pressure and a single acoustic signal receiver 20 capable of detecting acoustic pressure. A single receiver 20 is used to minimize the obstructions in environment 10 between source 18 and treatment 12. It is generally desirable for acoustic treatment 12 to absorb as much sound energy as possible while reflecting as little as possible. Thus, to evaluate the "worst case" performance of treatment 12, testing is carried out in the direction of most expected reflection. In terms of treatment 12, it will be assumed that the greatest sound reflection occurs when sound waves impinge thereon from a direction that is perpendicular to plane 16. Accordingly, source 18, receiver 20 and treatment 12 are placed in-line with one another along an imaginary line 22 that is perpendicular to plane 16. More specifically, source 18 is focused such that acoustic energy emitted therefrom in the form of a gated acoustic pulse 19 is directed substantially along line 22. For example, if source 18 is a directive speaker, this can be accomplished by facing the speaker at treatment 12.

Source 18 is separated from receiver 20 along line 22 by a distance D1 that is equal to at least one-half the wavelength of the frequency of acoustic pulse 19. Where a range of frequencies are to be tested, distance D1 is set for the lowest frequency of interest in order to accurately measure the incident wave. Receiver 20 is separated from plane 16 along line 22 by a distance $D_2$ that is equal to at least (t*c/2) where t is the length in time of gated acoustic pulse 19 and c is the speed of sound in environment 10, e.g., air. The distance $D_2$ is set to measure the reflected wave.

Acoustic performance testing in accordance with the present invention is carried out as follows. Gated acoustic pulse 19 is output from source 18 as described above and receiver 20 detects the acoustic pressure associated therewith. Pulse 19 continues to travel towards treatment 12 as indicated by arrow 24. While it is hoped that much or all of the energy of pulse 19 will be absorbed by treatment 12, it is expected that some will be reflected as indicated by arrow 26. Since distance $D_2$ is defined as described above, pulse 19 is complete before reflection 26 reaches receiver 20.

General free-field acoustic theory states that when an acoustic wave traveling in one medium (e.g., air) encounters the boundary of a second medium (e.g., treatment 12), part of the incident energy is reflected and part is dissipated (i.e., absorbed and/or transmitted therethrough). In terms of a typical acoustic treatment, the dissipated energy is primarily absorbed. Accordingly, the measure of acoustic performance of treatment 12 can be predicated upon a comparison (e.g., a ratio) between the acoustic pressure of pulse 19 and reflection 26. By utilizing a single receiver 20 to measure both of these acoustic pressures, the present invention eliminates any inconsistencies between measurement equipment while simultaneously minimizing unwanted obstructions in the measurement environment.

Figure 2:
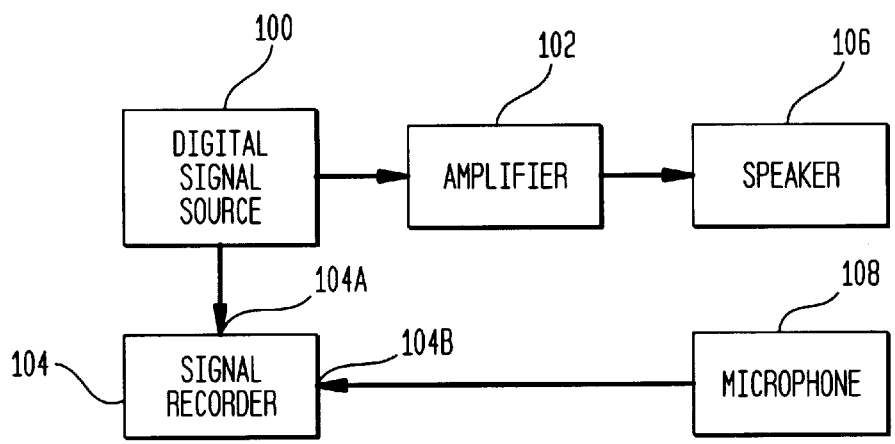
FIG. 2 is a schematic view of the instrumentation used in the present invention.

Referring now to FIG. 2, an instrumentation arrangement for carrying out the present invention is shown. A digital signal source 100 generates a gated signal pulse at a discrete frequency of interest. The pulse is fed to and amplified by an amplifier 102. The pulse is also supplied to the trigger input 104A of a signal recorder 104. That is, the leading edge of the gated signal pulse is used to start the recording process at recorder 104. The amplified pulse is supplied to a speaker 106 capable of reproducing the amplified pulse as the gated acoustic pulse at the discrete frequency. Speaker 106 is positioned/focused as described above with respect to source 18. To detect both the gated acoustic pulse 19 and its reflection 26, a microphone 108 is positioned as described above with respect to receiver 20. The output of microphone 108 is connected to a recording input 104B of recorder 104. Since the test setup guarantees that pulse 19 is complete before reflection 26 is received at receiver 20, recorder 104 records both pulse 19 and reflection 26 without overlap for ease of comparison.

Figure 3:
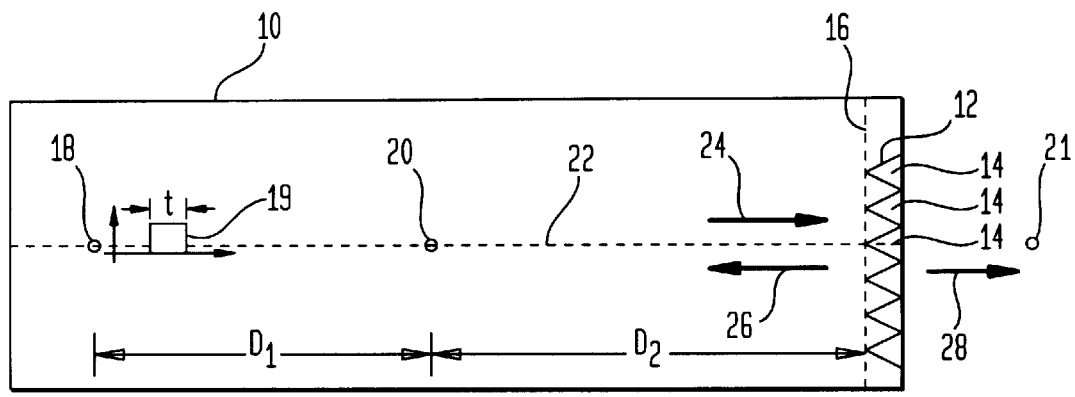
FIG. 3 is a schematic view of a test setup used to carry out acoustic performance testing according to another embodiment of the present invention.

Although it is generally sufficient to ignore any acoustic energy that may be transmitted through treatment 12 and out of environment 10, the test setup shown in FIG. 3 can be used if such transmission is of concern. More specifically, a second acoustic receiver 21 is positioned outside of environment 10 to detect acoustic energy transmitted through treatment 12 owing to pulse 19. Such transmitted energy is illustrated by arrow 28 and can be compared to and with pulse 19 and reflection 26 for evaluation of treatment 12.

The advantages of the present invention are numerous. Acoustic treatments can be performance tested across a broad range of discrete frequencies. Since the method and setup are not limited by frequency, acoustic treatments can be fully tested by a single test setup across all relevant frequencies such as from 80 to 40,000 hertz for acoustic treatments that are to be used in anechoic chambers.

It will be understood that many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. A method of acoustic testing, comprising the steps of:
providing a free-field acoustic environment;
disposing an acoustic treatment to be tested in said free-field acoustic environment;
generating a gated acoustic pulse from a source within said free-field acoustic environment, said gated acoustic pulse being of a frequency of interest;
focusing said gated acoustic pulse at said acoustic treatment, wherein said gated acoustic pulse is partially reflected from said acoustic treatment as reflected energy in said free-field acoustic environment;
measuring acoustic pressure of said gated acoustic pulse focused at said acoustic treatment from a location approximately in-line with said source and said acoustic treatment, said location being at least one-half wavelength of said frequency of interest away from said source and being at least a distance equal to (t*c/2) away from said acoustic treatment where t is equal to the duration of said gated acoustic pulse and c is equal to the speed of sound in said free-field acoustic environment;
measuring acoustic pressure of said reflected energy at said location; and
comparing said acoustic pressure of said reflected energy to said acoustic pressure of said gated acoustic pulse as an indication of performance of said acoustic treatment at said frequency of interest.

2. A method according to claim 1 wherein said free-field acoustic environment is an anechoic chamber, and wherein said step of disposing includes the step of incorporating said acoustic treatment as a wall of said anechoic chamber.

3. A method according to claim 1 wherein said frequency of interest lies between approximately 80 to 40,000 hertz.

4. A method according to claim 1 wherein said step of focusing includes the step of directing said gated acoustic pulse to approximately perpendicularly impinge upon a plane defined by said acoustic treatment.

5. A method according to claim 1 wherein said gated acoustic pulse is partially transmitted through said acoustic treatment, said method further comprising the step of measuring acoustic pressure of said gated acoustic pulse partially transmitted through said acoustic treatment, wherein said step of comparing includes the step of comparing said gated acoustic pulse partially transmitted through said acoustic treatment with said acoustic pressure of said reflected energy and said acoustic pressure of said gated acoustic pulse as an indication of performance of said acoustic treatment at said frequency of interest.

6. A method of acoustic testing, comprising the steps of:

providing a free-field acoustic environment;

disposing an acoustic treatment to be tested in said free-field acoustic environment;

generating a gated acoustic pulse from a source within said free-field acoustic environment, said Sated acoustic pulse being of a frequency of interest, said gated acoustic pulse having a leading edge;

focusing said gated acoustic pulse at said acoustic treatment, wherein said gated acoustic pulse is partially reflected from said acoustic treatment as reflected energy in said free-field acoustic environment;

positioning a microphone at a location approximately in-line with said source and said acoustic treatment, said location being at least one-half wavelength of said frequency of interest away from said source and being at least a distance equal to (t*c/2) away from said acoustic treatment where t is equal to the duration of said gated acoustic pulse and c is equal to the speed of sound in said free-field acoustic environment;

detecting acoustic pressure of said gated acoustic pulse with said microphone;

detecting acoustic pressure of said reflected energy with said microphone;

coupling a recorder to said microphone and to said source; and triggering said recorder to record said acoustic pressure of said gated acoustic pulse and said acoustic pressure of said reflected energy upon receipt of said leading edge of said gated acoustic pulse.

7. A method according to claim 6 wherein said free-field acoustic environment is an anechoic chamber, and wherein said step of disposing includes the step of incorporating said acoustic treatment as a wall of said anechoic chamber.

8. A method according to claim 6 wherein said frequency of interest lies between approximately 80 to 40,000 hertz.

9. A method according to claim 6 wherein said step of focusing includes the step of directing said gated acoustic pulse to approximately perpendicularly impinge upon a plane defined by said acoustic treatment.

10. A method according to claim 6 further comprising the step of comparing said acoustic pressure of said reflected energy to said acoustic pressure of said gated acoustic pulse as an indication of performance of said acoustic treatment at said frequency of interest.

11. A method according to claim 10 wherein said gated acoustic pulse is partially transmitted through said acoustic treatment, said method further comprising the steps of:

providing a second microphone on the opposite side of said acoustic treatment from said microphone; and detecting acoustic pressure of said gated acoustic pulse partially transmitted through said acoustic treatment using said second microphone, wherein said step of comparing includes the step of comparing said gated acoustic pulse partially transmitted through said acoustic treatment with said acoustic pressure of said reflected energy and said acoustic pressure of said gated acoustic pulse as an indication of performance of said acoustic treatment at said frequency of interest.

12. A system for testing an acoustic treatment, comprising:

an air-filled anechoic chamber for housing therein an acoustic treatment;

a signal source for generating a gated pulse at a frequency of interest;

a speaker coupled to said signal source and focused at the acoustic treatment for converting said gated pulse to a gated acoustic pulse at said frequency of interest, wherein said gated acoustic pulse is directed at the acoustic treatment and is partially reflected from the acoustic treatment as reflected energy in said anechoic chamber;

a microphone positioned at a location approximately in-line with said speaker and the acoustic treatment for detecting acoustic pressure of said reflected energy, said location being at least one-half wavelength of said frequency of interest away from said speaker and being at least a distance equal to (t*c/2) away from the acoustic treatment where t is equal to the duration of said gated acoustic pulse and c is equal to the speed of sound in air;

a recorder coupled to said microphone and to said signal source for recording said acoustic pressure of said gated acoustic pulse and said acoustic pressure of said reflected energy.

13. A system as in claim 12 wherein said speaker is focused to deliver said gated acoustic pulse such that said gated acoustic pulse impinges perpendicularly upon a plane defined by the acoustic treatment.

14. A system as in claim 12 further comprising a second microphone positioned on the opposite side of said acoustic treatment from said microphone.

* * * * *